United States Patent
Matsumura

(10) Patent No.: US 7,349,598 B2
(45) Date of Patent: Mar. 25, 2008

(54) SURFACE PLASMON RESONANCE DEVICE

(75) Inventor: Hajime Matsumura, Tokyo (JP)

(73) Assignee: Sony Corporation, Tokyo (JP)

( * ) Notice: Subject to any disclaimer, the term of this patent is extended or adjusted under 35 U.S.C. 154(b) by 70 days.

(21) Appl. No.: 11/076,819

(22) Filed: Mar. 10, 2005

(65) Prior Publication Data

US 2005/0201717 A1   Sep. 15, 2005

(30) Foreign Application Priority Data

Mar. 11, 2004   (JP)   ............................. 2004-069232

(51) Int. Cl.
*G02B 6/00* (2006.01)

(52) U.S. Cl. ........................................ 385/37; 385/147

(58) Field of Classification Search .................... None
See application file for complete search history.

(56) References Cited

U.S. PATENT DOCUMENTS

| | | | | |
|---|---|---|---|---|
| 4,583,818 | A * | 4/1986 | Chen et al. | 385/37 |
| 4,915,482 | A * | 4/1990 | Collins et al. | 359/276 |
| 6,613,594 | B1 * | 9/2003 | Lansford et al. | 438/16 |
| 6,870,624 | B2 * | 3/2005 | Hobbs et al. | 356/416 |
| 2001/0031503 | A1 * | 10/2001 | Challener et al. | 436/518 |
| 2002/0021445 | A1 * | 2/2002 | Bozhevolnyi et al. | 356/445 |
| 2003/0173501 | A1 * | 9/2003 | Thio et al. | 250/216 |
| 2004/0131001 | A1 * | 7/2004 | Nakada et al. | 369/112.27 |
| 2005/0035346 | A1 * | 2/2005 | Bazan et al. | 257/40 |
| 2005/0063045 | A1 * | 3/2005 | Sakahibara et al. | 359/361 |
| 2005/0269578 | A1 * | 12/2005 | Barnes et al. | 257/81 |

OTHER PUBLICATIONS

J. Ctyroky et al. Modelling of the surface plasmon resonance waveguide sensor with Bragg grating. Optical and Quantum Electronics, vol. 31, No. 9-10, pp. 927-941, Oct. 1999.*

L. Salomon et al. Near-field distribution of optical transmission of periodic subwavelength holes in a metal film. Physical Review Letters, vol. 86, No. 6, pp. 1110-1113, Feb. 2001.*

P.I. Nitikin et al. Chemical sensors based on surface plasmon resonance in Si grating structures. Transducers '97, 1997 International Conference on Solid-State Sensors and Actuators, pp. 1359-1362, Jun. 1997.*

* cited by examiner

*Primary Examiner*—Sung Pak
*Assistant Examiner*—Mike Stahl
(74) *Attorney, Agent, or Firm*—Wolf, Greenfield & Sacks, P.C.

(57) ABSTRACT

A surface plasmon resonance device of the present invention includes a transparent medium layer and a conductive layer, a periodic structure being present at the interface therebetween. Assuming that the wavelength of visible light incident on the conductive layer through the transparent medium layer is $\lambda$ (nm), the periodicity of the periodic structure is $(\lambda/633) \times 100$ nm to $(\lambda/633) \times 500$ nm, and the amplitude of the periodic structure is $(\lambda/633) \times 5$ nm to $(\lambda/633) \times 20$ nm. For example, when $\lambda=633$ nm, the periodicity of the periodic structure is 100 nm to 500 nm, and the amplitude is 5 nm to 20 nm.

17 Claims, 13 Drawing Sheets

SURFACE PLASMON RESONANCE DEVICE

BACKGROUND OF THE INVENTION

1. Field of the Invention

The present invention relates to a surface plasmon resonance device, and particularly to a surface plasmon resonance device suitably used for measuring the dielectric constants of various samples.

2. Description of the Related Art

A conventional known method for measuring the dielectric constant of a surface of a sample is a surface plasmon resonance method (for example, Japanese Unexamined Patent Application Publication No. 11-271215). Among modes of plasmons referring to collective resonance of free electrons present in a conductive material such as a metal or the like, the conventional method uses a surface plasmon mode in which plasmons are localized at a surface of the conductive material. The principle of measurement is as follows: Surface plasmons are coupled with an electromagnetic wave in a dielectric material at an interface between the dielectric material and a conductive material such as a metal or the like. The mode of the electromagnetic wave in the dielectric material changes due to the influence of a change in the dielectric constant of the dielectric material, and the propagation of plasmons in the conductive material such as metal or the like changes with frequencies. Therefore, a change in dielectric constant of a dielectric sample can be read as a change in frequency of the surface plasmon mode.

However, when an interface between a dielectric material and a conductive material such as a metal or the like is planar, an electromagnetic wave propagating in the dielectric material cannot be coupled with the plasmons in the conductive material. This phenomenon will be described below on the basis of a metal as an example of a conductive material. FIG. 12 is a schematic view of a metal-dielectric interface, and FIG. 13 shows a dispersion relation of surface plasmons in the system shown in FIG. 12. In FIG. 13, a component of the wavenumber of the plasmons parallel to the interface is shown as abscissa $k_x$, and the frequency of the plasmons is shown as ordinate $\omega$. The dispersion relation of the surface plasmons is shown by a solid line and represented by the following equation:

$$k_x = \frac{\omega}{c}\sqrt{\frac{\varepsilon_d \varepsilon(\omega)}{\varepsilon_d + \varepsilon(\omega)}}$$

wherein $\varepsilon_d$ is the dielectric constant of a dielectric material, and $\varepsilon(\omega)$ is the dielectric constant of a metal.

$\varepsilon(\omega)$ is represented by the following equation:

$$\varepsilon(\omega) = \varepsilon_\infty - \left(\frac{\omega_p}{\omega}\right)^2$$

wherein $\varepsilon_\infty$ is a constant, and $\omega_p$ is the plasma frequency of a bulk metal. The frequency of surface plasmons is saturated at a high wavenumber $k_x$, and asymptotically approaches a dotted line shown by $\omega = \omega_{sp}$ in FIG. 13, the dotted line being represented by the following equation:

$$\omega_{sp} = \frac{\omega_p}{\sqrt{\varepsilon_\infty + \varepsilon_d}}$$

Among electromagnetic waves present in the dielectric material, an electromagnetic wave whose propagation direction is parallel to the interface has a dispersion curve shown by a broken line in FIG. 13. This line is in contact with a dispersion curve of surface plasmons at the origin, and is represented by the following equation:

$$k_x = \frac{\omega}{c}\sqrt{\varepsilon_d}$$

The dispersion relation of an electromagnetic wave in a dielectric material is generally represented by the following equation:

$$k_x^2 + k_z^2 = \left(\frac{\omega}{c}\right)^2 \varepsilon_d$$

wherein $k_z$ is a component of the wavenumber of plasmons vertical to the interface. Among electromagnetic waves in the dielectric material, an electromagnetic wave showing a dispersion curve lying above the broken line in FIG. 13 has a real number $k_z$ and propagates in the z direction shown in FIG. 12. On the other hand, an electromagnetic wave showing a dispersion curve lying below the broken line in FIG. 13 has a pure imaginary number $k_z$ and attenuates in the z direction shown in FIG. 12 to cause so-called evanescent light. Since a wavenumber component $k_z$ parallel to the interface is kept by applying a connection condition for an electromagnetic wave at the interface, the electromagnetic wave coupled with surface plasmons in the dielectric material is limited to an electromagnetic wave showing a dispersion relation lying below the broken line in FIG. 13, i.e., evanescent light.

As described above, an electromagnetic wave which can be coupled with surface plasmons is limited to evanescent light attenuating at a metal surface. Therefore, some consideration is required for exciting surface plasmons by optical means. In a method for exciting surface plasmons, a metal is formed in a thin film, and light is incident on the side opposite to the side in contact with a dielectric sample. Therefore, a three-layer structure comprising a dielectric sample, a metal layer, and a transparent medium is generally used for exciting surface plasmons. FIG. 14 is a schematic drawing of this structure. As the transparent medium, for example, glass or plastics, is frequently used because visible light is used in ordinary measurement. The metal layer is thin (for example, about 50 nm) enough to permit visible light incident on one side to reach the other side.

Japanese Unexamined Patent Application Publication No. 6-50883 proposes a surface plasmon resonance measuring device comprising, without using a movable part, a block having a surface which internally reflects an electromagnetic radiation beam transmitted therethrough, a periodic structure layer disposed on the surface of the block, and a conductive layer provided on the periodic structure layer. However, in this document, the periodic structure layer is not described in detail.

However, for a sample having a higher dielectric constant than that of a transparent medium, the dielectric constant cannot be measured by the above-mentioned method. This will be described below. FIGS. 15 and 16 show dispersion relations of surface plasmons appearing in the system shown in FIG. 14. There are two types of surface plasmons corresponding to the two types of interfaces including the metal-dielectric sample interface and the metal-transparent medium interface present in the system shown in FIG. 14, and the surface plasmons are localized at each interface. In FIGS. 15 and 16, the frequencies of both types of surface plasmons are saturated at high wavenumbers $k_x$, and gradually approach the dotted lines ($\omega=\omega_{sp}^d$, $\omega=\omega_{sp}^g$) in FIGS. 15 and 16. The value of each of the dotted lines is as follows:

$$\omega_{sp}^d = \frac{\omega_p}{\sqrt{\varepsilon_\infty + \varepsilon_d}}, \omega_{sp}^g = \frac{\omega_p}{\sqrt{\varepsilon_\infty + \varepsilon_g}}$$

wherein $\varepsilon_g$ is the dielectric constant of the transparent medium. In each of FIGS. 15 and 16, a broken line is a tangent to a dispersion curve of surface plasmons at the metal-transparent medium interface at the origin. Identically to the above, a dispersion curve of an electromagnetic wave propagating in the transparent medium lies above the broken line. On the other hand, evanescent light in the transparent medium shows a dispersion curve lying below the broken line.

FIG. 15 shows the case in which the dielectric constant $\varepsilon_d$ of the dielectric material is lower than the dielectric constant $\varepsilon_g$ of the transparent medium. In this case, the following relation is established:

$$\omega_{sp}^d > \omega_{sp}^g$$

Therefore, the dispersion curve of surface plasmons at the metal-dielectric sample interface partially lies above the broken line. Thus, an electromagnetic wave propagating in the transparent medium can be coupled with surface plasmons at the metal-dielectric sample interface. Consequently, the dielectric constant of the sample can be measured by applying light at an appropriate frequency to the transparent medium layer.

On the other hand, FIG. 16 shows the case in which the dielectric constant $\varepsilon_d$ of the dielectric is higher than the dielectric constant $\varepsilon_g$ of the transparent medium. In this case, the following relation is established:

$$\omega_{sp}^d < \omega_{sp}^g$$

Therefore, the dispersion curve of surface plasmons at the metal-dielectric sample interface entirely lies below the broken line. Thus, an electromagnetic wave propagating in the transparent medium cannot be coupled with surface plasmons at the metal-dielectric sample interface. Consequently, there is the problem that the dielectric constant of the sample cannot be measured with light incident on the transparent medium layer.

SUMMARY OF THE INVENTION

Accordingly, it is an object of the present invention to provide a surface plasmon resonance device capable of measuring the dielectric constant of a dielectric material, the dielectric constant being higher than that of a transparent medium layer.

In order to achieve the object, the present invention provides a surface plasmon resonance device comprising a transparent medium layer and a conductive layer, a periodic structure being present at the interface therebetween, wherein assuming that the wavelength of visible light incident on the conductive layer through the transparent medium layer is λ (nm), the periodicity of the periodic structure is (λ/633)×100 nm to (λ/633)×500 nm.

For example, when λ=633 nm, the periodicity of the periodic structure is 100 nm to 500 nm. The amplitude of the periodic structure is preferably (λ/633)×5 nm to (λ/633)×20 nm, and more preferably (λ/633)×5 nm to (λ/633)×10 nm or (λ/633)×10 nm to (λ/633)×20 nm. For example, when λ=633 nm, the amplitude of the periodic structure is 5 nm to 10 nm or 10 nm to 20 nm.

As the material for the conductive layer, various materials can be used as long as they have free electrons at a concentration sufficient to generate surface plasmons. More specifically, metals such as gold, silver, and the like; semi-metals; semiconductors; and the like can be used. The periodic structure can be formed by, for example, burying a plurality of micro structures comprising a conductive material such as a metal or the like in a transparent medium, or filling a transparent medium in a plurality of pores formed in a film of a conductive material.

In the invention having the above-mentioned construction, the interface between the transparent medium layer and the conductive layer has the periodic structure having a periodicity of (λ/633)×100 nm to (λ/633)×500 nm depending on the wavelength λ of the used visible light. Therefore, even when a dielectric sample to be measured has a higher dielectric constant than that of the transparent medium layer, an electromagnetic wave propagating in the transparent medium layer is strongly coupled with surface plasmons at the interface between the conductive layer and the dielectric sample.

In the present invention, even when a dielectric sample has a higher dielectric constant than that of the transparent medium layer, an electromagnetic wave propagating in the transparent medium layer is strongly coupled with surface plasmons at the interface between the conductive layer and the dielectric sample, thereby permitting measurement of the higher dielectric constant of the dielectric sample than that of the transparent medium layer.

DESCRIPTION OF THE PREFERRED EMBODIMENTS

Figure 1:
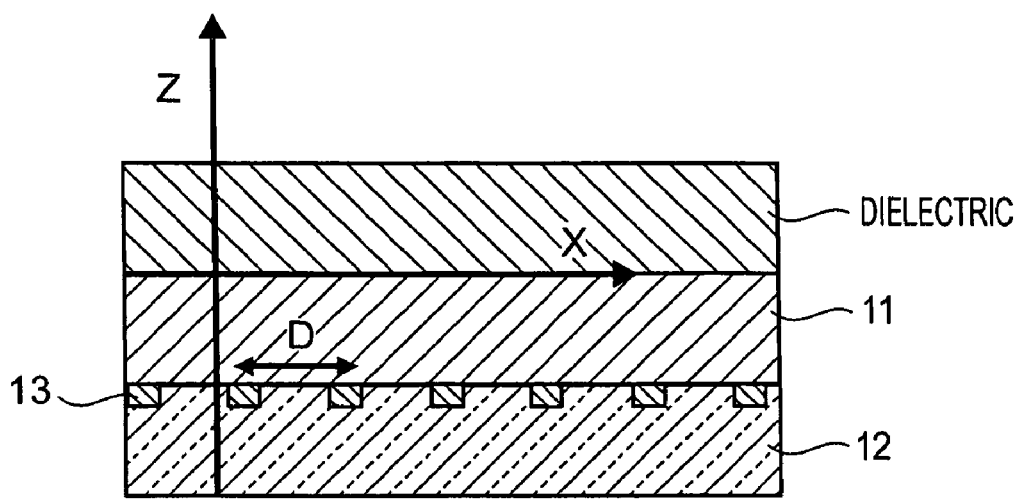
FIG. 1 is a sectional view showing a principal portion of a surface plasmon resonance device according to an embodiment of the present invention.

An embodiment of the present invention will be described below with reference to the drawings. In all drawings of the embodiment, the same or corresponding portions are denoted by the same reference numeral.

FIG. 1 shows a principal portion of a surface plasmon resonance device according to the embodiment.

As shown in FIG. 1, the surface plasmon resonance device has a periodic structure 13 disposed at the interface between a metal layer 11 and a transparent medium layer 12 serving as a light propagation layer. The metal layer 11 is thin enough to permit visible light incident on one of the sides of the metal layer 11 to reach the other side. For example, when the metal layer 11 comprises gold, the thickness is about 50 nm.

Figure 2:
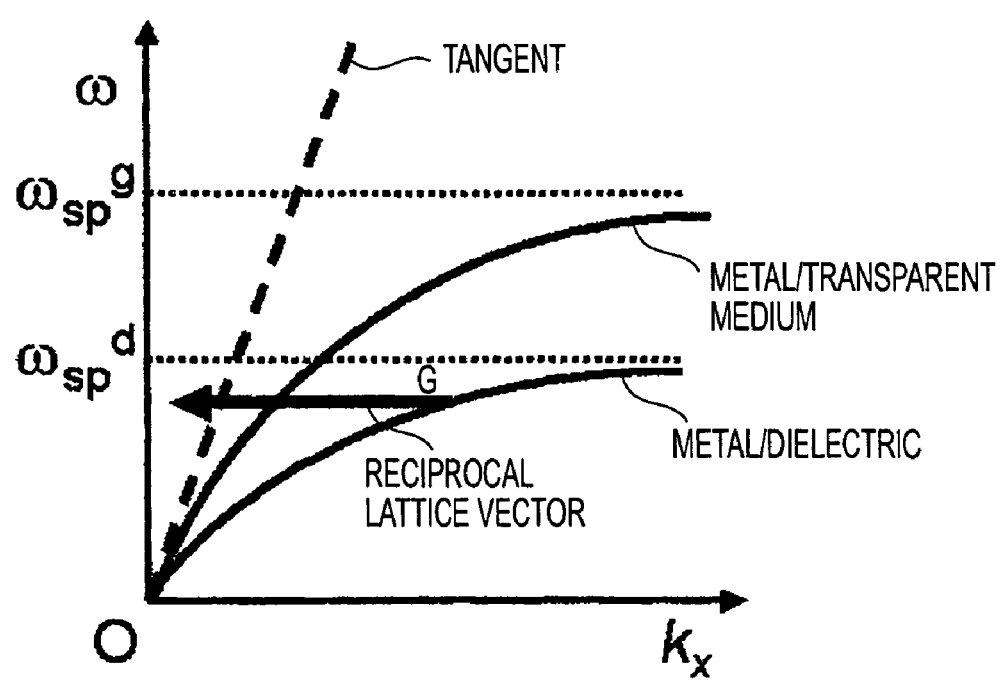
FIG. 2 is a schematic diagram showing dispersion curves of surface plasmons in the surface plasmon resonance device according to the embodiment of the present invention.

The periodic structure 13 has the function to couple the surface plasmons at the interface between the metal layer 11 and a dielectric material (to be measured) with an electromagnetic wave propagating in the transparent medium layer 12. Namely, in the presence of a periodic structure at an interface, two electromagnetic waves are generally equivalent when having wavenumbers different by an amount corresponding to an integral multiple of the reciprocal lattice vector of the periodic structure. Therefore, as shown in FIG. 2, when a dispersion curve of surface plasmons can be moved in parallel by an integral multiple of the reciprocal lattice vector of the periodic structure 13 so that the dispersion curve lies above the broken line, the surface plasmons at the interface between the metal layer 11 and the dielectric material can be coupled with an electromagnetic wave propagating in the transparent medium layer 12. The magnitude of the reciprocal lattice vector is represented by the equation below using the periodicity D of the periodic structure 13.

$$G = \frac{2\pi}{D}$$

Figure 3:
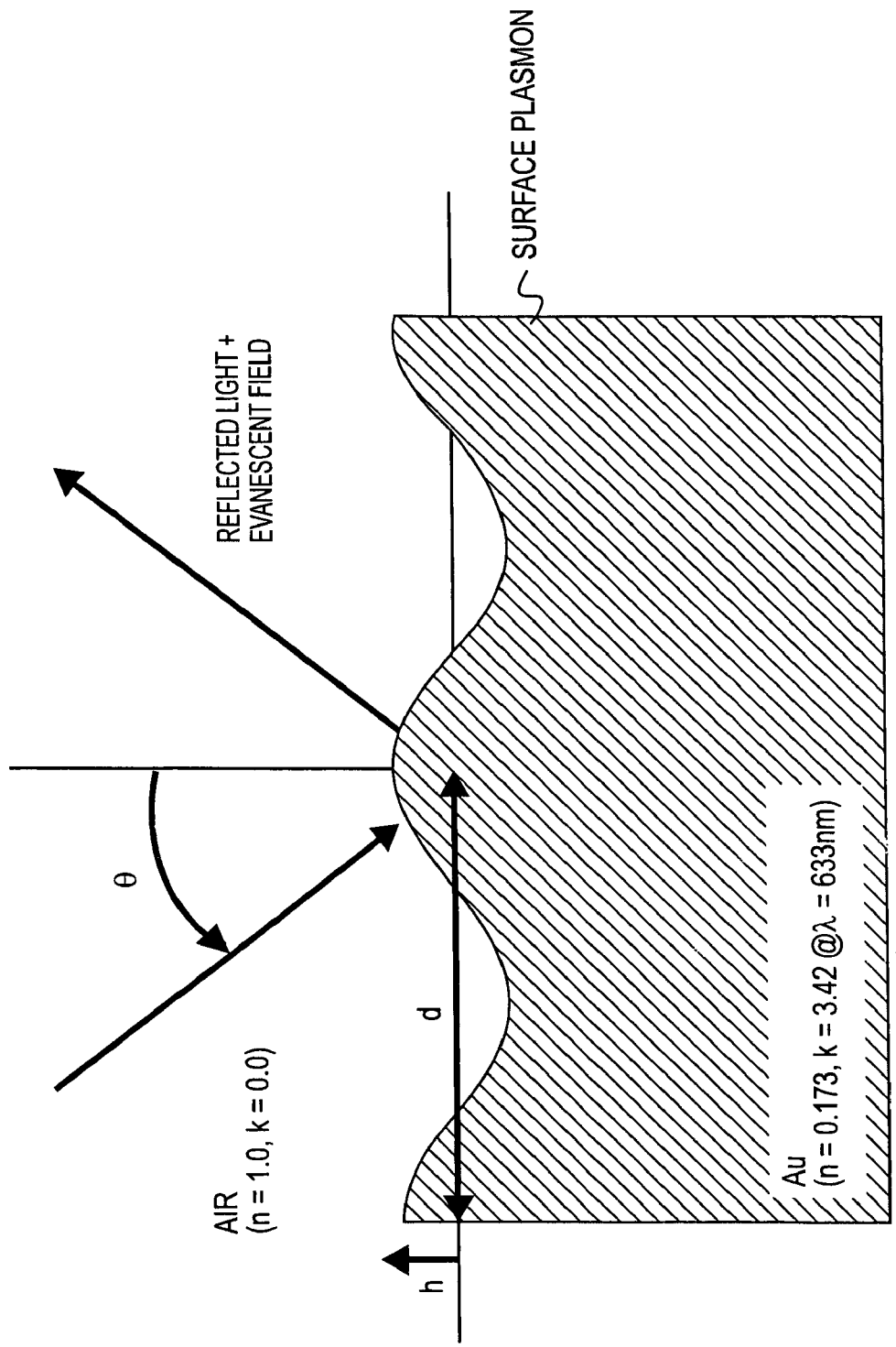
FIG. 3 is a schematic diagram showing the model used in simulation for evaluating a periodic structure in the surface plasmon resonance device according to the embodiment of the present invention.

The plasma frequency of a metal generally used for surface plasmon resonance, for example, gold or silver, is the order of $10^{14}$ Hz to $10^{15}$ Hz, and the corresponding wavelength is μm to sub μm (for example, 1 μm to 0.1 μm). Therefore, the maximum periodicity of the periodic structure 13 is preferably the above-described order. The periodicity is more preferably selected as follows:

FIGS. 3 to 9 shows the results of simulation performed for evaluating the periodic structure 13 used in the surface plasmon resonance device. FIG. 3 shows a model used for the simulation. Although data about coupling between propagating light and evanescent light at a semi-infinite gold (Au) surface having a periodic structure is shown here for convenience of calculation, the essential is not impaired. The periodicity of the periodic structure is denoted by d, and the amplitude is denoted by h. As incident light, He—Ne laser light at a wavelength λ of 633 nm is used. When a complex refractive index is represented by n-ik, Au has n=0.173 and k=3.42, and air has n=1.0 and k=0.0 at λ=633 nm. The angle θ of incidence of light is represented by θ.

Figure 4:
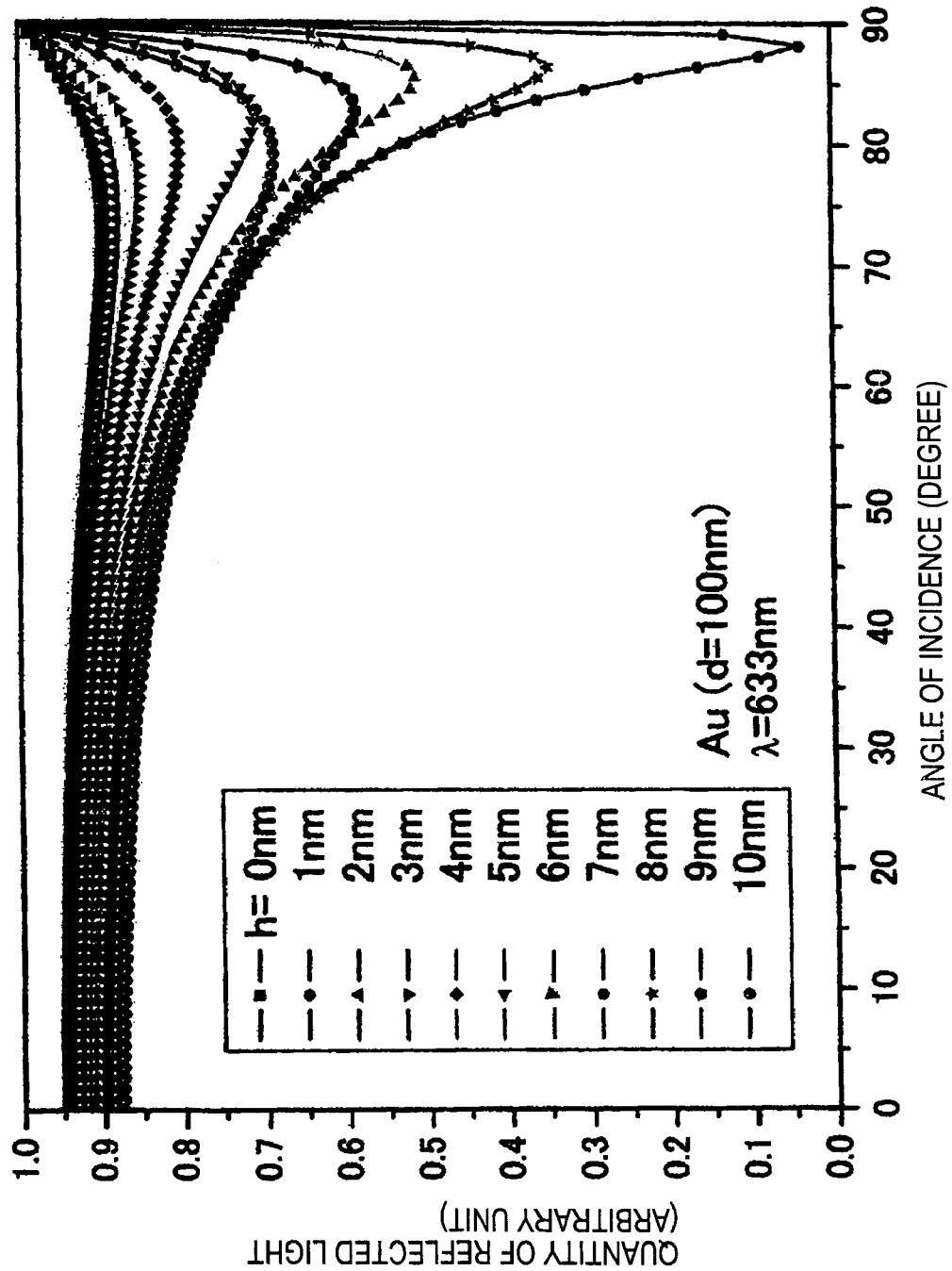
FIG. 4 is a schematic diagram showing the results of simulation for evaluating the periodic structure in the surface plasmon resonance device according to the embodiment of the present invention.

FIG. 4 shows changes in quantity of reflected light (arbitrary unit) with the angle θ of incidence when h was changed from 0 nm to 10 nm at intervals of 1 nm and d was 100 nm. FIG. 4 indicates that with h of 5 to 10 nm, the quantity of light rapidly decreases in a range of θ from 80° to 90°. This shows that surface plasmons are strongly coupled with evanescent light in the range.

Figure 5:
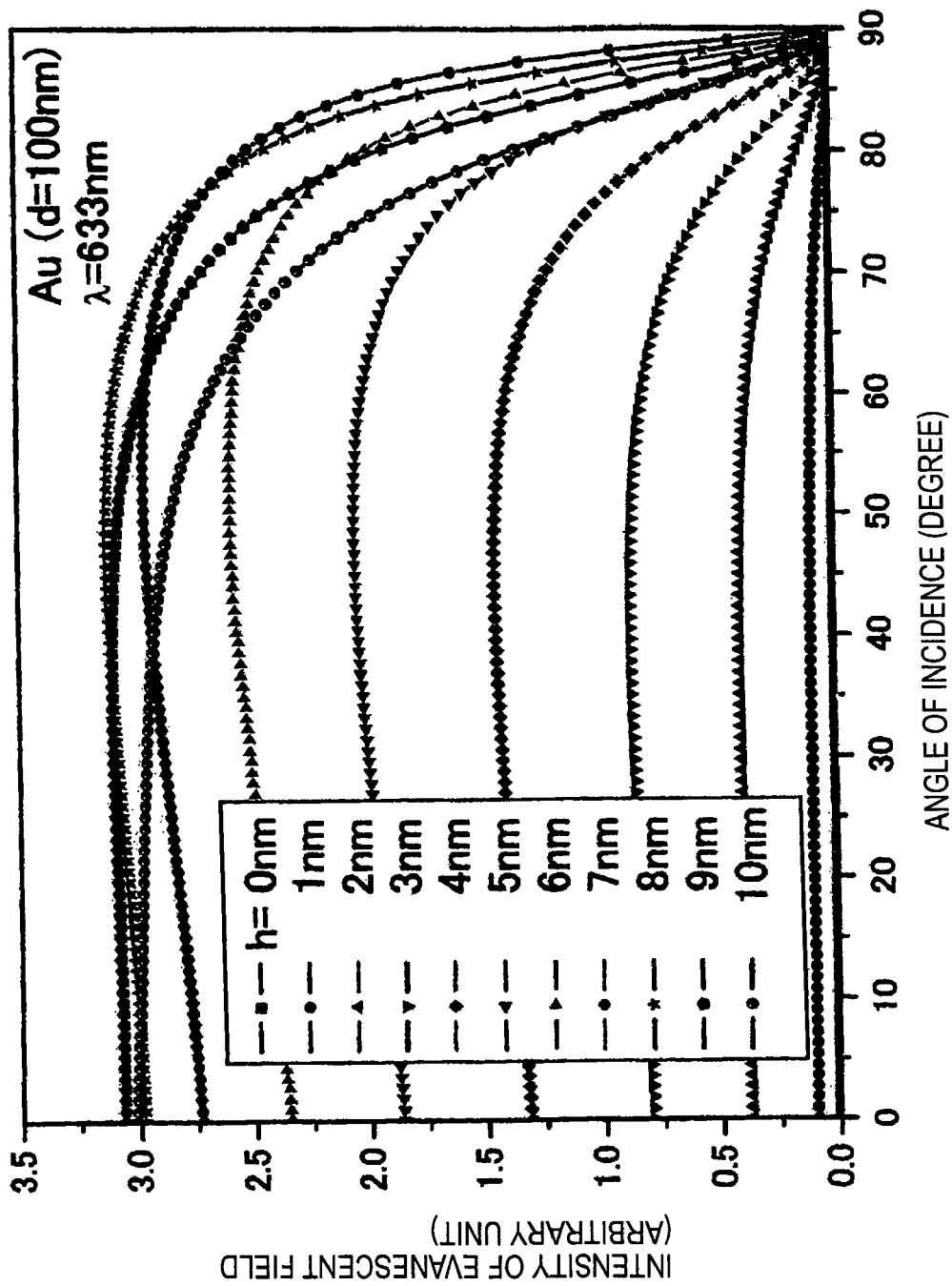
FIG. 5 is a schematic diagram showing the results of simulation for evaluating the periodic structure in the surface plasmon resonance device according to the embodiment of the present invention.

FIG. 5 shows changes in intensity of evanescent field (arbitrary unit) with the angle θ of incidence when h was changed from 0 nm to 10 nm at intervals of 1 nm and d was 100 nm. FIG. 5 indicates that with h of 5 nm to 10 nm, the evanescent field is enhanced.

Figure 6:
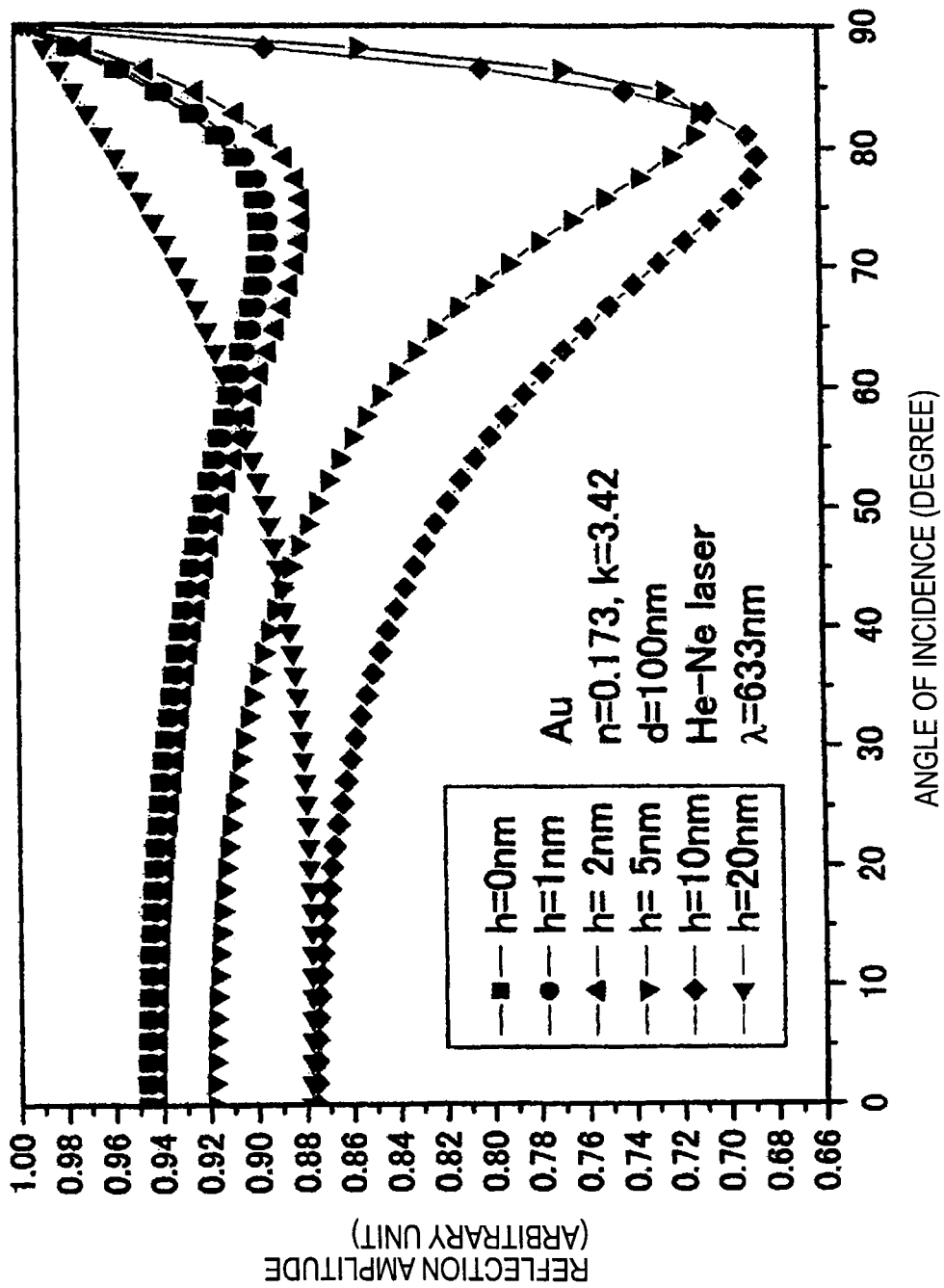
FIG. 6 is a schematic diagram showing the results of simulation for evaluating the periodic structure in the surface plasmon resonance device according to the embodiment of the present invention.

FIG. 6 shows changes in amplitude of reflected light (arbitrary unit) with the angle θ of incidence when h was changed from 0 nm to 1 nm, 2 nm, 5 nm, 10 nm, and 20 nm. FIG. 6 indicates that with h of 5 nm to 10 nm, the amplitude abruptly decreases in correspondence with FIG. 4.

Figure 7:
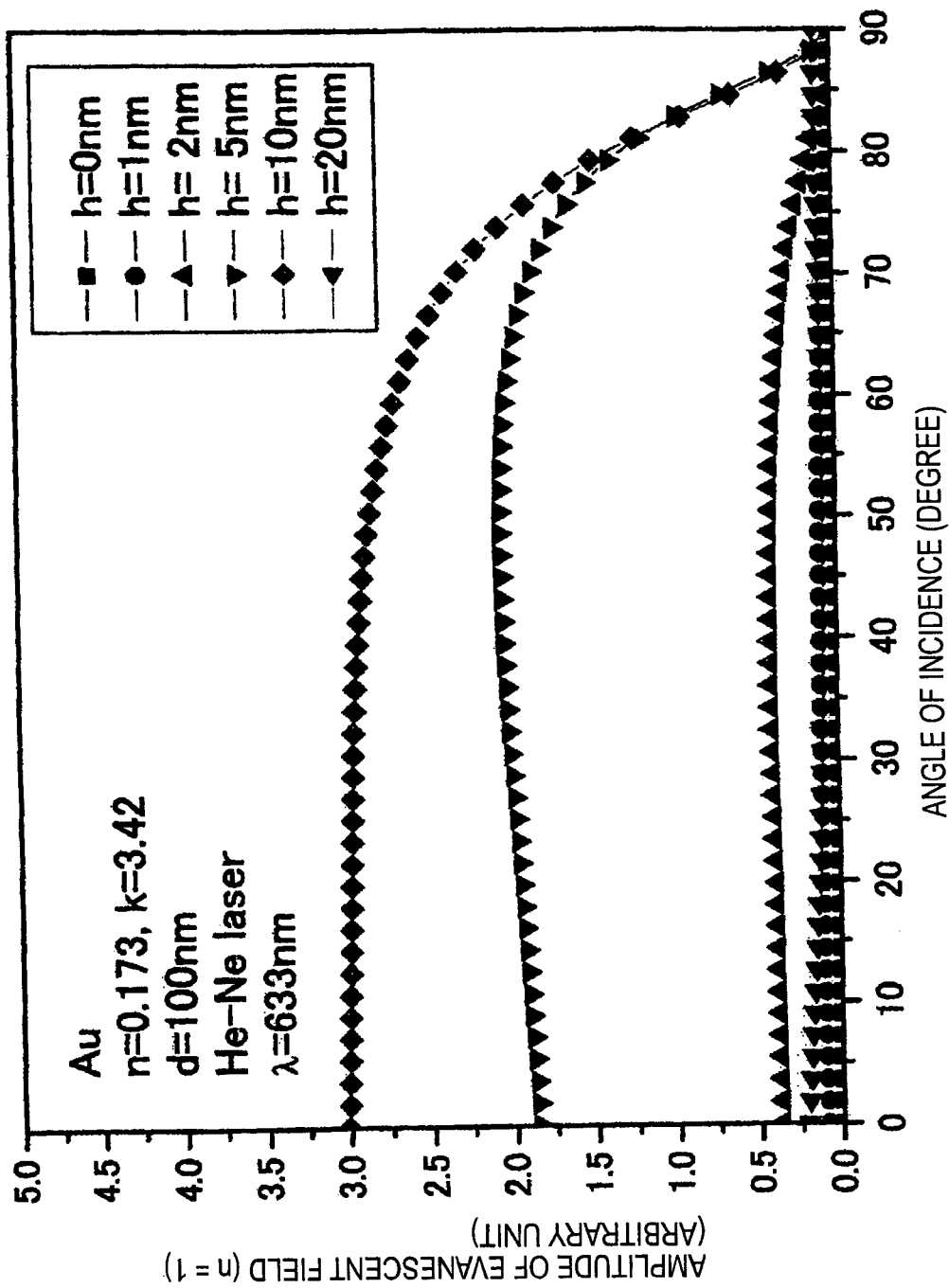
FIG. 7 is a schematic diagram showing the results of simulation for evaluating the periodic structure in the surface plasmon resonance device according to the embodiment of the present invention.

FIG. 7 shows changes in amplitude of evanescent light (arbitrary unit) with the angle θ of incidence when h was changed from 0 nm to 1 nm, 2 nm, 5 nm, 10 nm, and 20 nm. FIG. 7 indicates that with h of 5 nm to 10 nm, the evanescent field is abruptly enhanced in correspondence with FIG. 5.

Figure 8:
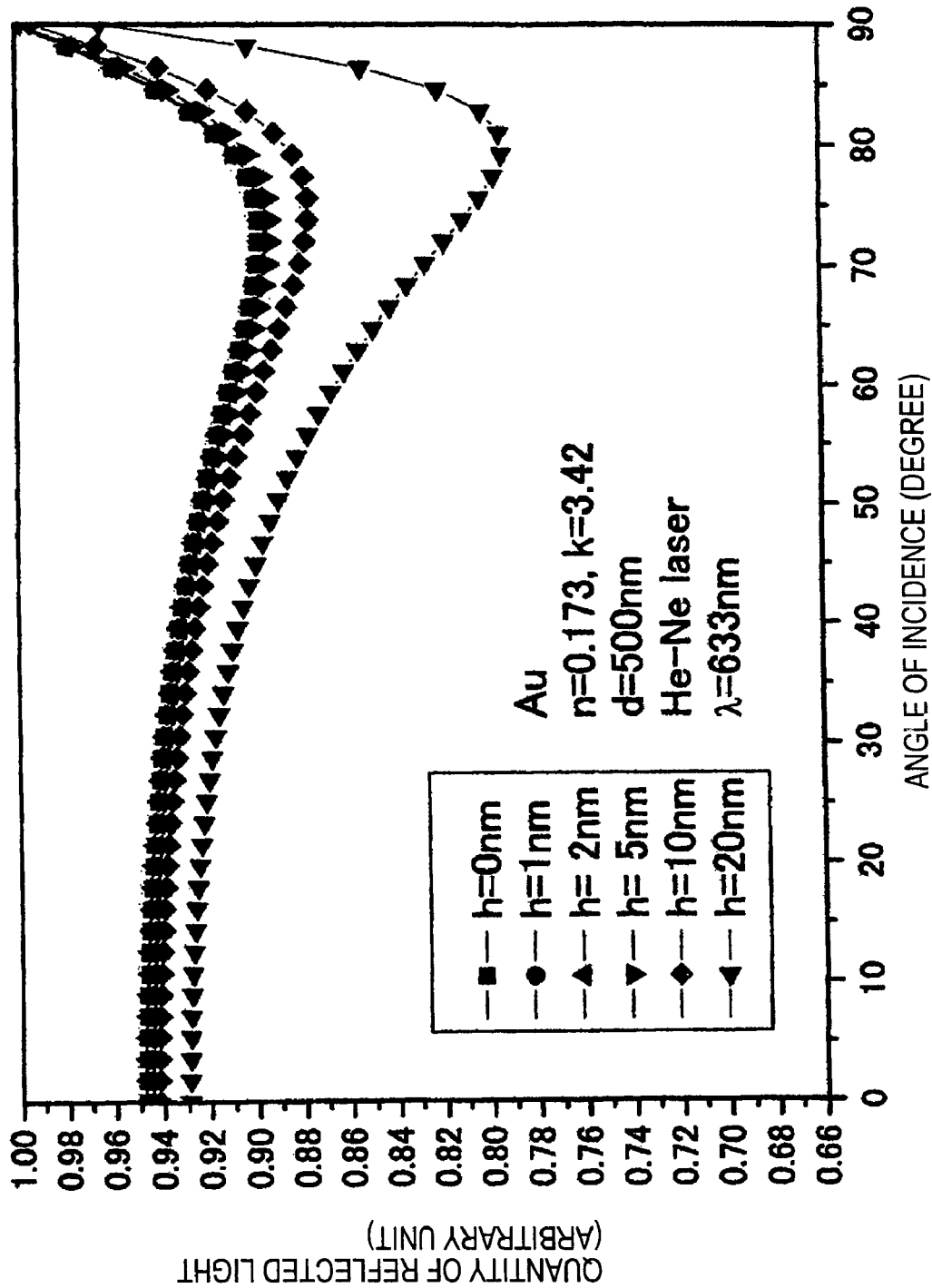
FIG. 8 is a schematic diagram showing the results of simulation for evaluating the periodic structure in the surface plasmon resonance device according to the embodiment of the present invention.

FIG. 8 shows changes in quantity of reflected light (arbitrary unit) with the angle θ of incidence when h was changed from 0 nm to 1 nm, 2 nm, 5 nm, 10 nm, and 20 nm and d was 500 nm. In this case, with h of 10 to 20 nm, the quantity of light rapidly decreases in a range of θ from about 70° to 800°. This shows that surface plasmons are strongly coupled with evanescent light in this region.

Figure 9:
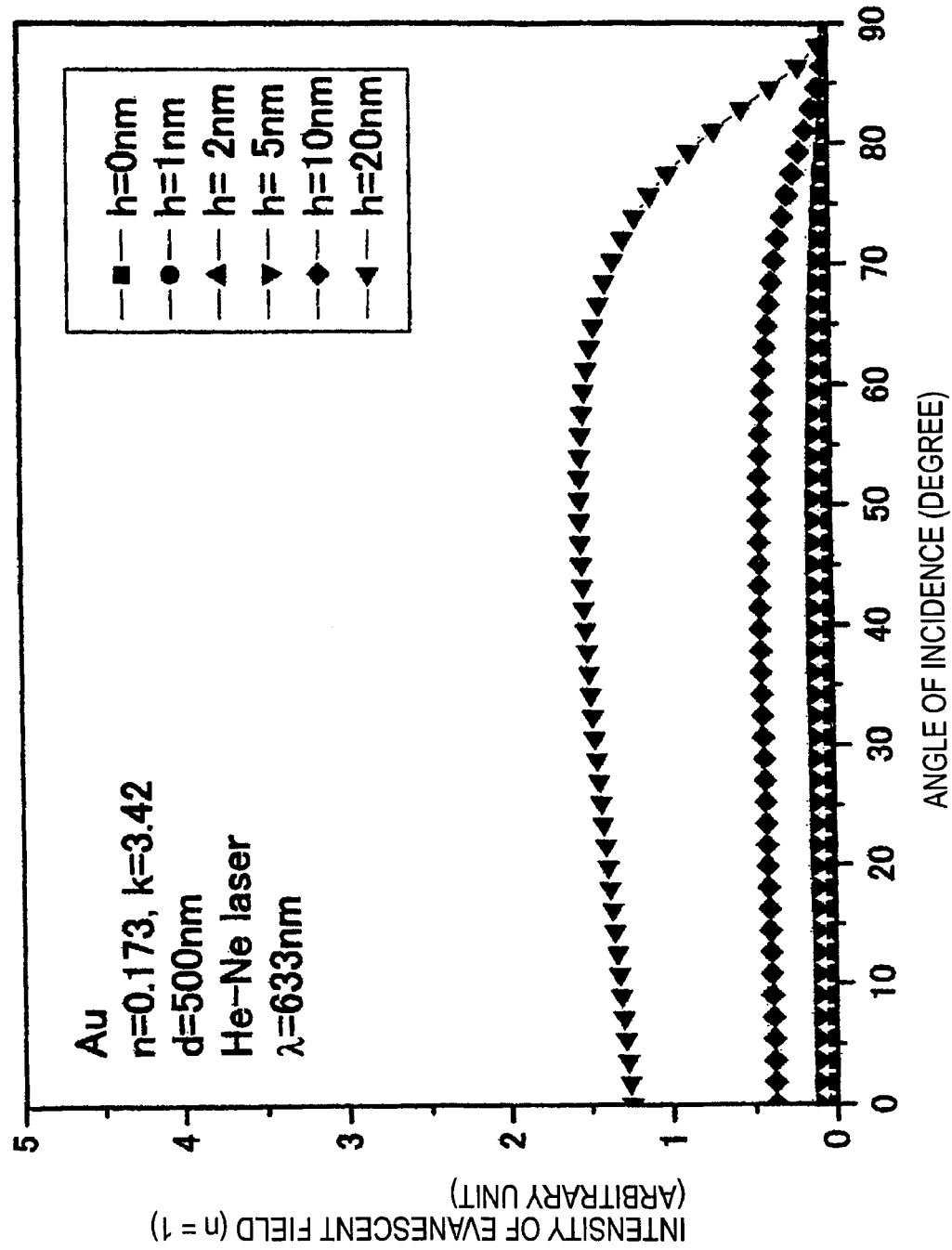
FIG. 9 is a schematic diagram showing the results of simulation for evaluating the periodic structure in the surface plasmon resonance device according to the embodiment of the present invention.

FIG. 9 shows changes in intensity of evanescent field (arbitrary unit) with angle θ of incidence when h was changed from 0 nm to 1 nm, 2 nm, 5 nm, 10 nm, and 20 nm and d was 500 nm. FIG. 9 indicates that with h of 10 nm to 20 nm, the evanescent field is enhanced.

According to the above results, it can be said that with d of 100 nm to 500 nm and h of 5 mm to 20 nm, surface plasmons are strongly coupled with evanescent light. Although the above results are obtained with $\lambda=633$ nm, it is generally thought that surface plasmons are strongly coupled with evanescent light when d=($\lambda$/633)×100 nm to ($\lambda$/633)×500 nm and h=($\lambda$/633)×5 nm to ($\lambda$/633)×20 nm wherein $\lambda$ is a wavelength in the visible region (for example, wavelength of 360 nm to 830 nm).

Each of the metal layer 11 and the transparent medium layer 12 can be formed in any one of various shapes. For example, the metal layer 11 may be formed in a cylindrical shape, and the transparent medium layer 12 may be provided outside the metal layer 11. As the transparent medium layer 12, a triangular prism may be used like in a publicly known surface plasmon resonance device.

The present invention will be described with reference to examples.

EXAMPLE 1

Figure 10:
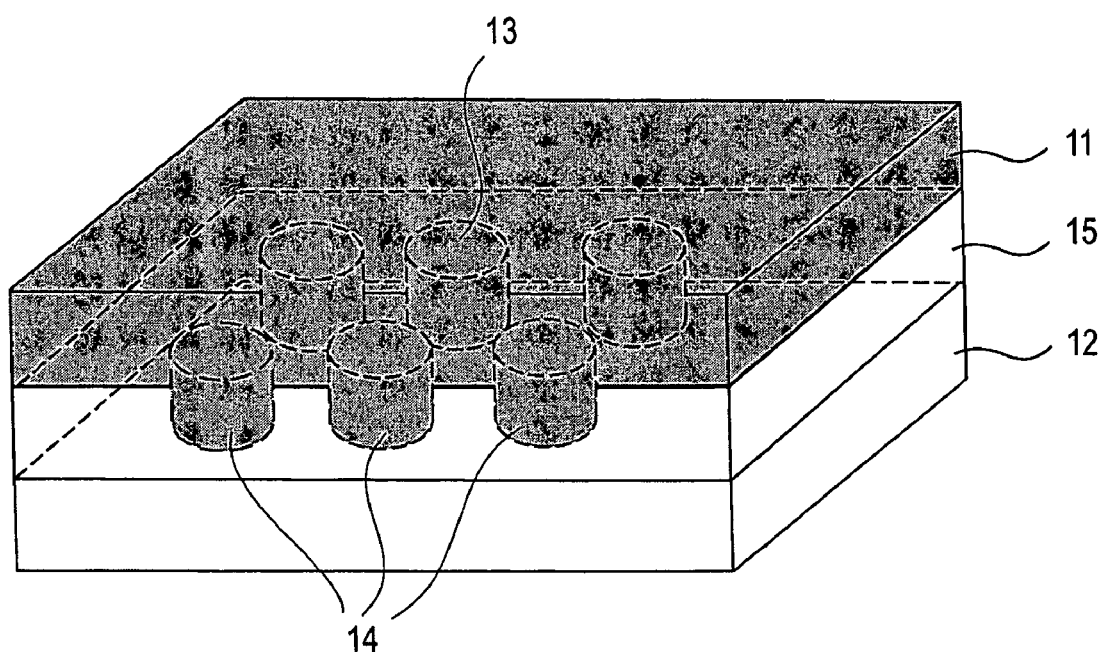
FIG. 10 is a schematic diagram showing an example of the surface plasmon resonance device according to the embodiment of the present invention.

FIG. 10 shows a surface plasmon resonance device of Example 1. As shown in FIG. 10, the surface plasmon resonance device uses a glass substrate as a transparent medium layer 12, and micro structures 14 each comprising a gold fine particle or a micro cylinder are periodically buried in the transparent medium layer 15 comprising, for example, glass or a material having the same dielectric constant as that of glass, thereby forming a periodic structure 13. The micro structures 14 can be formed by, for example, micro patterning or a template using phase separation (for example, a nano-template formed by spreading a polystyrene/polyisoprene block copolymer on a substrate to form a sea island-like micro phase-separation structure, and then removing the polyisoprene by ozone oxidative decomposition to form nano-pores). Furthermore, a gold thin film is formed as a metal layer 11 on the transparent medium layer 15. The gold thin film can easily be formed by vapor deposition, sputtering, or the like.

The material constituting the transparent medium layer 12 is not limited to glass, and any one of other materials transparent in the visible region, for example, plastics and the like, may be used. The material constituting the micro structures 14 is not limited to gold, and any one of other metals such as silver, platinum, and the like may be used.

EXAMPLE 2

Figure 11:
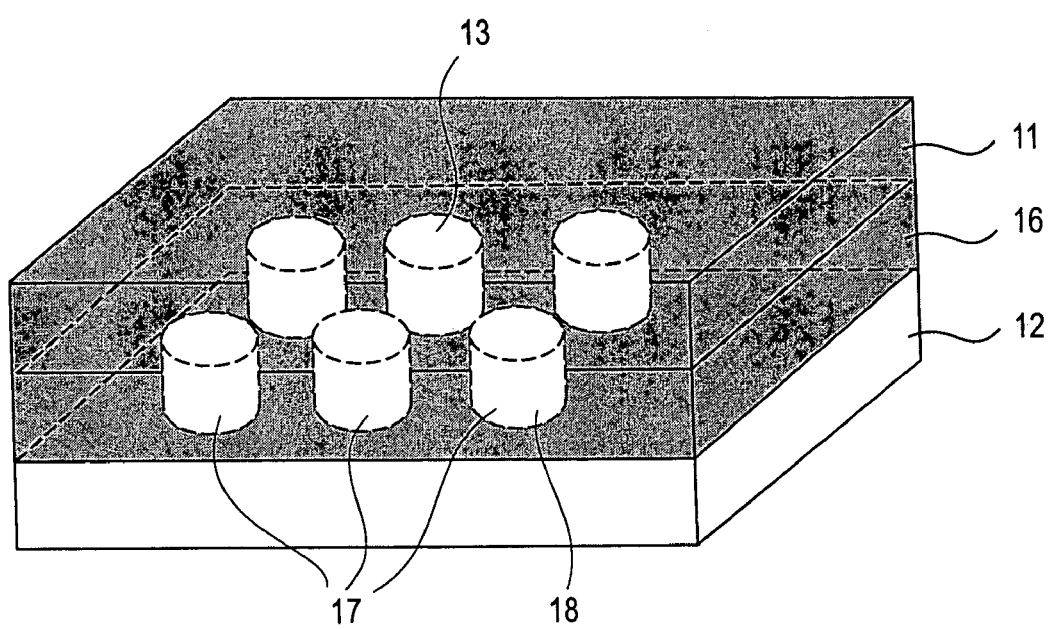
FIG. 11 is a schematic diagram showing another example of the surface plasmon resonance device according to the embodiment of the present invention.
Figure 12:
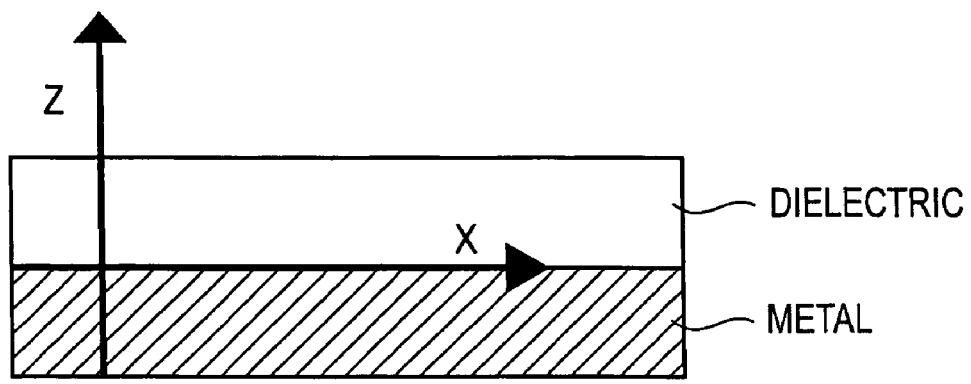
FIG. 12 is a sectional view showing a principal portion of a conventional surface plasmon resonance device.
Figure 13:
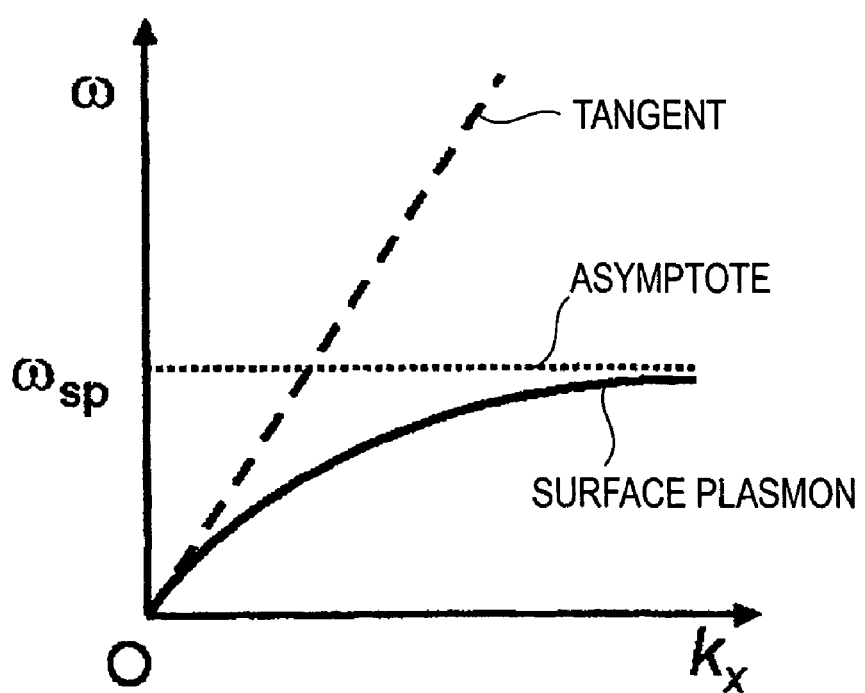
FIG. 13 is a schematic diagram showing a dispersion curve of surface plasmons in a conventional surface plasmon resonance device.
Figure 14:
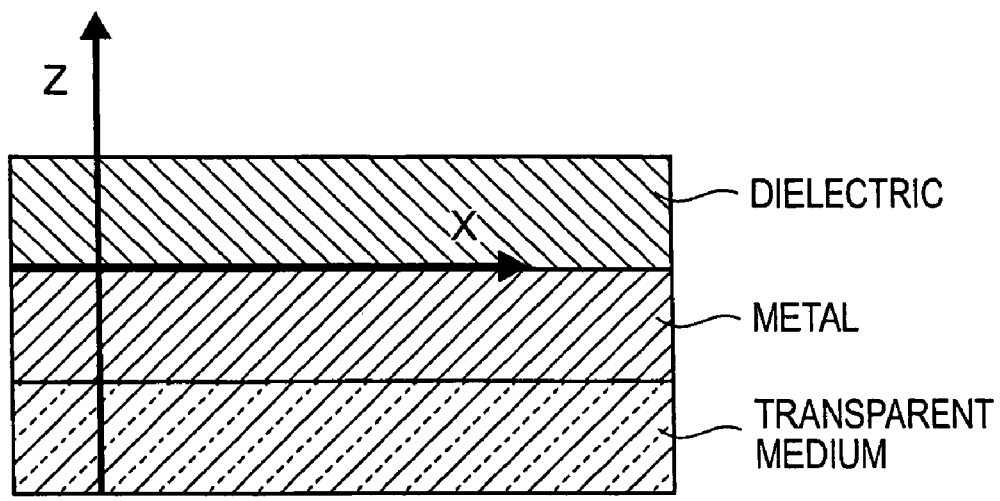
FIG. 14 is a sectional view showing a principal portion of another conventional surface plasmon resonance device.
Figure 15:
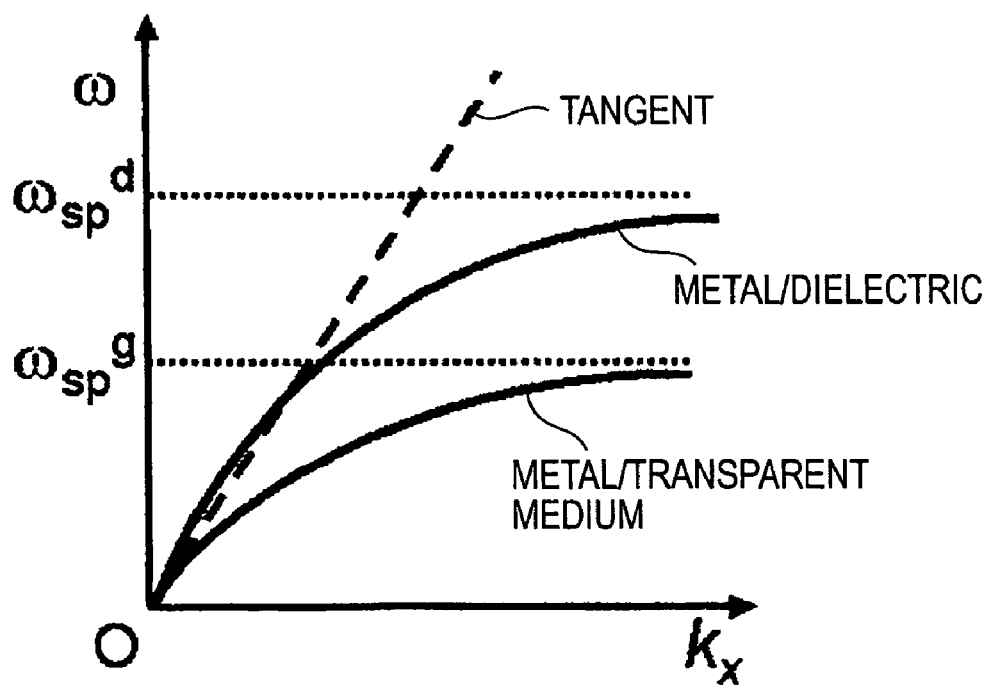
FIG. 15 is a schematic diagram showing dispersion curves of surface plasmons in another conventional surface plasmon resonance device.
Figure 16:
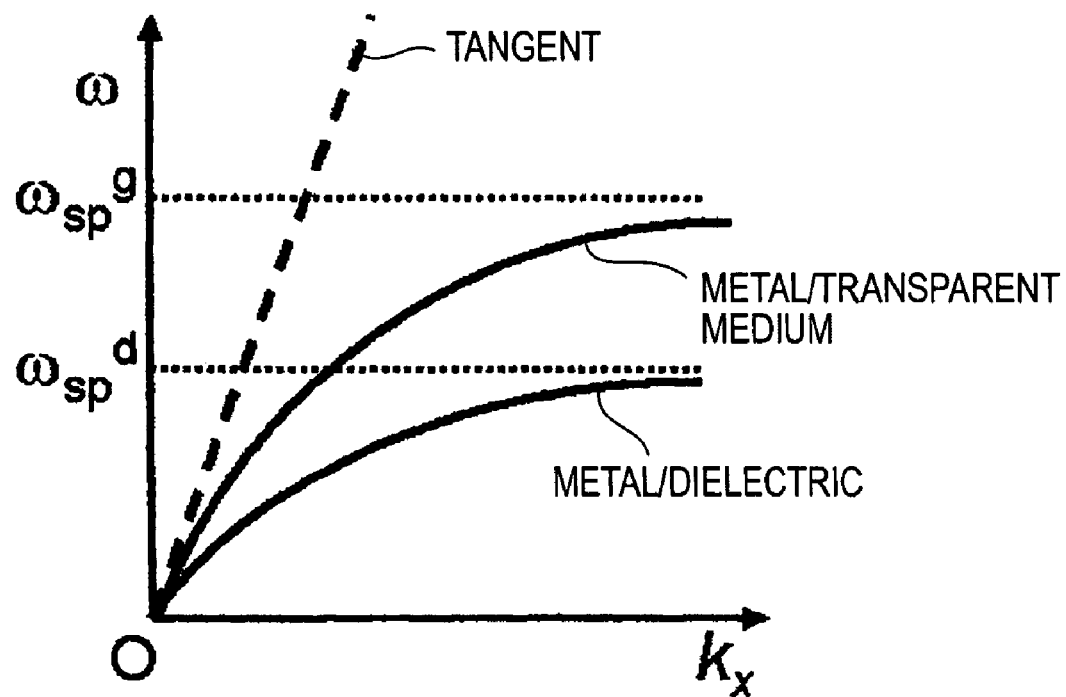
FIG. 16 is a schematic diagram showing dispersion curves of surface plasmons in still another conventional surface plasmon resonance device.

FIG. 11 shows a surface plasmon resonance device of Example 2. As shown in FIG. 11, the surface plasmon resonance device comprises a glass substrate used as a transparent medium layer 12, and a gold thin film 16 formed thereon. Furthermore, pores 17 are periodically formed in the gold thin film 16, the pores 17 being filled with glass or a transparent medium layer 18 having the same dielectric constant as that of glass to form a periodic structure 13. The pores 17 can be easily formed by irradiating the gold thin film 16 with an electron beam or the like. Furthermore, a gold thin film is formed as a metal layer 11 on the gold thin film 16. The gold thin film can be easily formed by vapor deposition, sputtering, or the like.

The material constituting the transparent medium layer 12 is not limited to glass, and any one of other materials transparent in the visible region, for example, plastics and the like, may be used. The material constituting the micro structures 14 is not limited to gold, and any one of other metals such as silver, platinum, and the like may be used.

Although the embodiment and examples of the present invention are described in detail above, the present invention is not limited to the embodiment and examples, and various changes can be made on the basis of the technical idea of the present invention.

For example, the numerical values, structures, materials, and processes described above in the embodiment and examples are only examples, and the numerical values, structures, materials, and processes may be changed according to demand.

What is claimed is:

1. A surface plasmon resonance device comprising a transparent medium layer and a conductive layer, a periodic structure of varying height being present at the interface therebetween, wherein the conductive layer is thin enough to permit visible light incident on a first side of the conductive layer to reach a second side of the conductive layer, wherein, assuming that the wavelength of visible light incident on the conductive layer through the transparent medium layer is $\lambda$ (nm), the periodicity of the periodic structure is between about ($\lambda$/633)×100 nm and ($\lambda$/633)×500 nm;
    wherein the amplitude of the height of the periodic structure is between about ($\lambda$/633)×5 nm and ($\lambda$/633)×10 nm.

2. A surface plasmon resonance device comprising a transparent medium layer and a conductive layer, a periodic structure of varying height being present at the interface therebetween, wherein the conductive layer is thin enough to permit visible light incident on a first side of the conductive layer to reach a second side of the conductive layer, wherein, assuming that the wavelength of visible light incident on the conductive layer through the transparent medium layer is $\lambda$ (nm), the periodicity of the periodic structure is between about ($\lambda$/633)×100 nm and ($\lambda$/633)×500 nm;
    wherein the amplitude of the height of the periodic structure is between about 5 nm and 10 nm.

3. A surface plasmon resonance device comprising a transparent medium layer and a conductive layer, a periodic structure of varying height being present at the interface therebetween, wherein the conductive layer is thin enough to permit visible light incident on a first side of the conductive layer to reach a second side of the conductive layer, wherein, assuming that the wavelength of visible light incident on the conductive layer through the transparent medium layer is $\lambda$ (nm), the periodicity of the periodic structure is between about ($\lambda$/633)×100 nm and ($\lambda$/633)×500 nm;
    wherein the amplitude of the height of the periodic structure is between about 10 nm and 20 nm.

4. The surface plasmon resonance device according to any of claims 1, 2, or 3, wherein the periodicity of the periodic structure is 100 nm to 500 nm.

5. The surface plasmon resonance device according to any of claims 2 or 3, wherein the amplitude of the height of the periodic structure is between about ($\lambda$/633)×5 nm and ($\lambda$/633)×20 nm.

6. The surface plasmon resonance device according to any of claims 2 or 3, wherein the amplitude of the height of the periodic structure is between about ($\lambda$/633)×10 nm and ($\lambda$/633)×20 nm.

7. The surface plasmon resonance device according to any of claims 1, 2, or 3, wherein the conductive layer comprises a metal.

8. The surface plasmon resonance device according to any of claims 1, 2, or 3, wherein the periodic structure comprises a plurality of micro structures each comprising a conductive material, the micro structures being buried in a transparent medium.

9. The surface plasmon resonance device according to claim 8, wherein the conductive material is a metal.

10. The surface plasmon resonance device according to any of claims 1, 2, or 3, wherein the periodic structure comprises a plurality of pores formed in a film of a conductive material, the pores being filled with a transparent medium.

11. The surface plasmon resonance device according to any of claims 1, 2, or 3, wherein the surface plasmon resonance device is used for measuring a dielectric sample having a higher dielectric constant than that of the transparent medium layer.

12. The surface plasmon resonance device of any of claims 1, 2, or 3, wherein the conductive layer has a thickness that is less than or equal to about 50 nm.

13. The surface plasmon resonance device of claim 12, wherein the conductive layer comprises a metal layer.

14. The surface plasmon resonance device of claim 13, wherein the metal layer comprises gold.

15. The surface plasmon resonance device of any of claims 1, 2, or 3, wherein a first side of the conductive layer contacts the transparent medium layer and a second side of the conductive layer contacts a material for which a material property is measured using the visible light.

16. The surface plasmon resonance device of any of claims 1, 2, or 3, wherein the transparent medium layer comprises glass.

17. The surface plasmon resonance device of any of claims 1, 2, or 3, wherein the transparent medium layer comprises plastic.

* * * * *